United States Patent [19]

Bouzard et al.

[11] 4,234,721
[45] Nov. 18, 1980

[54] PROCESS FOR THE PREPARATION OF THE CRYSTALLINE MONOHYDRATE OF 7-[D-AMINO-(P-HYDROXYPHENYL-)ACETAMIDO)-3-METHYL-3-CEPHEN-4-CARBOXYLIC ACID

[75] Inventors: Daniel Bouzard, Franconville; Abraham Weber; Jacques Stemer, both of Paris, all of France

[73] Assignee: Bristol-Myers Company, New York, N.Y.

[21] Appl. No.: 71,951

[22] Filed: May 21, 1979

Related U.S. Application Data

[62] Division of Ser. No. 874,457, Feb. 2, 1978, Pat. No. 4,160,863, which is a division of Ser. No. 785,392, Apr. 7, 1977, abandoned.

[30] Foreign Application Priority Data

Apr. 27, 1976 [GB] United Kingdom ............... 17028/76

[51] Int. Cl.³ ................. C07D 501/02; C07D 501/12; C07D 501/22
[52] U.S. Cl. ................................................. 544/30
[58] Field of Search ......................................... 544/30

[56] References Cited

U.S. PATENT DOCUMENTS

| | | | |
|---|---|---|---|
| Re. 29,164 | 3/1977 | Crast, Jr. ................................ | 544/30 |
| 3,489,752 | 1/1970 | Crast, Jr. ................................ | 544/30 |
| 3,781,282 | 12/1973 | Garbrecht ............................ | 544/30 |
| 3,957,773 | 5/1976 | Burton et al. ......................... | 544/30 |
| 3,985,741 | 10/1976 | Crast, Jr. et al. ..................... | 544/30 |

FOREIGN PATENT DOCUMENTS 829758 6/1974 Belgium .
1240687 7/1971 United Kingdom .

OTHER PUBLICATIONS

Dunn et al. T. Antibiotics 24, 65–80 (1976).
Marconi et al. Chem Abs. 83, 145764a (1975).

*Primary Examiner*—Mark L. Berch
*Attorney, Agent, or Firm*—Robert E. Carnahan; Robert H. Uloth

[57] ABSTRACT

A novel crystalline monohydrate of 7-[D-α-amino-α-(p-hydroxyphenyl)acetamido]-3-methyl-3-cephem-4-carboxylic acid is prepared and found to be a stable useful form of the cephalosporin antibiotic especially advantageous for pharmaceutical formulations.

17 Claims, 1 Drawing Figure

INFRARED SPECTRUM OF CEFADROXIL MONOHYDRATE

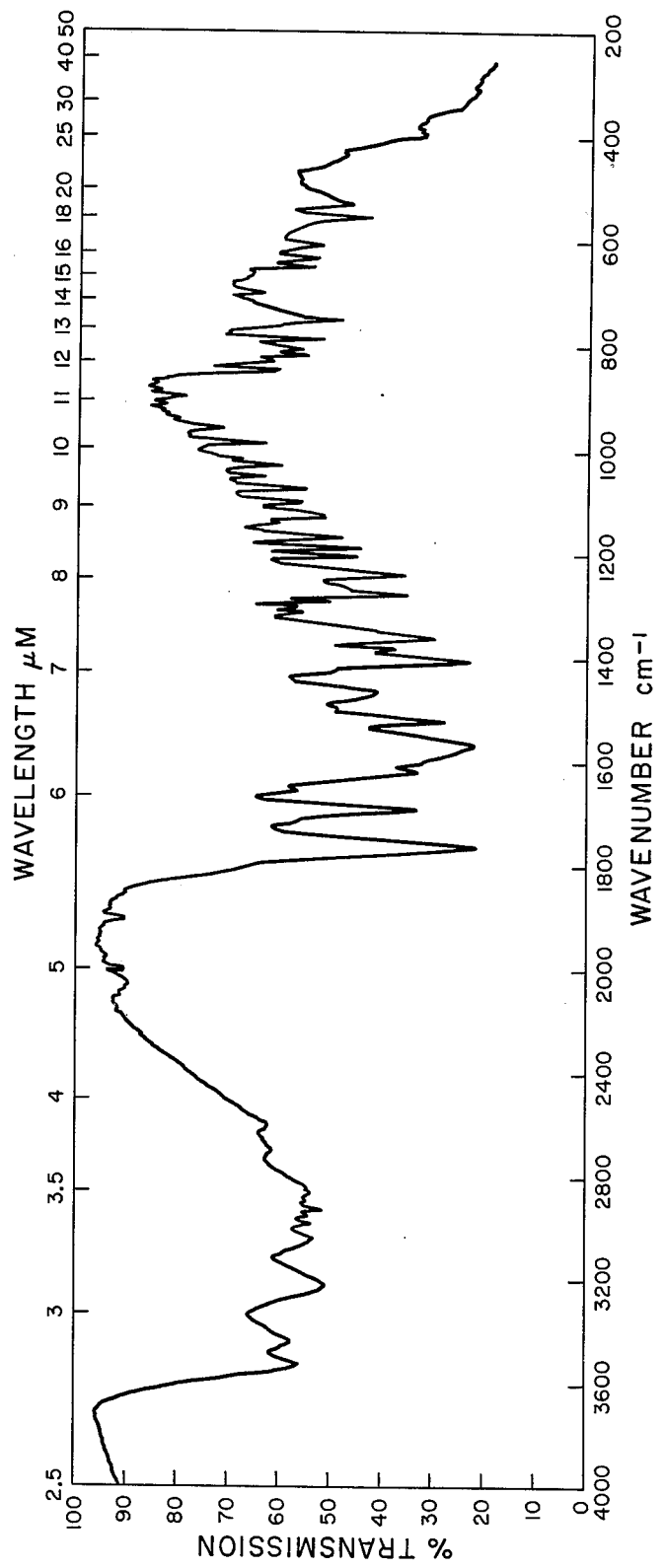

PROCESS FOR THE PREPARATION OF THE CRYSTALLINE MONOHYDRATE OF 7-[D-AMINO-(P-HYDROXYPHENYL)ACETAMIDO)-3-METHYL-3-CEPHEN-4-CARBOXYLIC ACID

CROSS-REFERENCE TO RELATED APPLICATION

This is a division of co-pending application Ser. No. 874,457, filed Feb. 2, 1978, now U.S. Pat. No. 4,160,863, which is a division of Ser. No. 785,392, filed Apr. 7, 1977, and now abandoned.

BACKGROUND OF THE INVENTION

1. Field of the Invention

The crystalline cephalosporin monohydrate of the present invention possesses in general the usual attributes of that family of antibacterial agents and is particularly useful in pharmaceutical formulations for treatment of bacterial infections by oral administration.

2. Description of the Prior Art

The cephalosporin compound 7-[D-α-amino-α-(p-hydroxyphenyl)acetamido]-3-methyl-3-cephem-4-carboxylic acid is disclosed and claimed in U.K. Pat. No. 1,240,687 (see also U.S. Pat. No. 3,489,752). The above-named compound has been given the generic name cefadroxil and has the structural formula

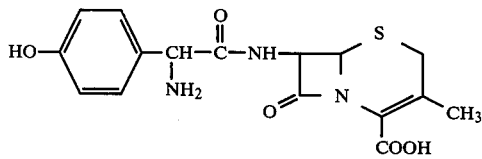

Cefadroxil is active as a broad spectrum antibiotic effective in controlling diseases caused by a wide variety of Gram-positive and Gram-negative microorganisms. It is of particular interest as an oral cephalosporin antibiotic.

U.K. Pat. No. 1,240,687 discloses the preparation of cefadroxil by acylation of 7-aminodesacetoxycephalosporanic acid (7-ADCA) with an amino-protected derivative of D(—)-α-amino-α-(p-hydroxyphenyl)acetic acid. Of the various amino-protected acylating agents disclosed, the highest yields were obtained with D-(—)-α-(p-hydroxypheny)-α-(t-butoxycarbonylamino)acetic acid via the so-called t-BOC method. The yields in this process, however, were not as high as are desired for commercial production and the reagent used in the t-BOC process is very expensive.

U.S. Pat. No. 3,985,741 discloses preparation of cefadroxil by acylation of 7-ADCA with the mixed anhydride of D-(—)-α-(p-hydroxyphenyl)glycine when the latter's α-amino group has been blocked with a β-keto compound such as methyl acetoacetate. This process, while having certain definite advantages over the t-BOC procedure, is still not as efficient as is desired for a commercially feasible production process.

Production of cefadroxil by enzymatic hydrolysis of its O-acetyl derivative is described in Belgium Pat. No. 829,758.

U.S. Pat. No. 3,781,282 discloses in a teaching example (Example 7) the preparation of cefadroxil by dissolution of a cefadroxil.DMF solvate in acidified water followed by neutralization with triethylamine. There is no indication from this reference that the cefadroxil product would be in the form of a crystalline monohydrate or indeed that it would even be in a crystalline form.

In view of the many important advantages of cefadroxil, it is desirable to have a commercially useful process for preparing this antibiotic in higher yields and with lower production costs than afforded by the prior art processes. Additionally, it is desirable to provide cefadroxil in a stable crystalline form such as a crystalline hydrate which would enable the antibiotic to be prepared into suitable pharmaceutical formulations for antibacterial use.

SUMMARY OF THE INVENTION

The present invention provides a novel crystalline monohydrate of cefadroxil and processes for preparing said monohydrate. Also provided is an improved acylation process for preparing cefadroxil which results in excellent product yields and lower production costs when compared with prior art processes.

DESCRIPTION OF THE DRAWING

The accompanying drawing, FIG. 1, illustrates the characteristic infrared absorption spectrum of cefadroxil monohydrate as obtained by the procedures described herein when determined in a potassium bromide pellet.

DETAILED DESCRIPTION OF THE INVENTION

According to one aspect, the present invention provides an improved process for preparing cefadroxil, or a pharmaceutically acceptable salt thereof, which process comprises (a) silylating 7-aminodesacetoxycephalosporanic acid in an inert substantially anhydrous aprotic solvent;

(b) acylating the so-produced silylated 7-aminodesacetoxycephalosporanic acid with D(—)-α-amino-α-(p-hydroxyphenyl)acetyl chloride hydrochloride in an inert substantially anhydrous aprotic solvent in the presence of an acid acceptor;

(c) cleaving any silyl groups of the acylation product by hydrolysis or alcoholysis; and (d) recovering the desired cephalosporanic acid, or a pharmaceutically acceptable salt thereof.

The pharmaceutically acceptable salts referred to above include, for example, (1) non-toxic pharmaceutically acceptable salts of the acidic carboxylic acid group such as the sodium, potassium, calcium, aluminium and ammonium salts and nontoxic substituted ammonium salts with amines such as tri(lower)alkylamines, procaine, dibenzylamine, N-benzylbeta-phenethylamine, 1-ephenamine, N,N'-dibenzylethylenediamine, dehydrobietylamine, N,N'-bisdehydroabietylethylenediamine, N-(lower)alkylpiperidines, such as N-ethylpiperidine and other amines which have been used to form salts of benzyl-penicillin; and (2) nontoxic pharmaceutically acceptable acid addition salts (i.e., salts of the basic nitrogen) such as (a) the mineral acid addition salts such as hydrochloride, hydrobromide, hydroiodide, sulfate, sulfamate, sulfonate, phosphate, etc. and (b) the organic acid addition salts such as the maleate, acetate, citrate, tartrate, oxalate, succinate, benzoate, fumarate, malate, mandelate, ascorbate, β-naphthalene sulfonate and p-toluenesulfonate. As used herein the term "(lower)alkyl" is defined as including straight and branched chain saturated hydrocarbon radicals having from 1 to 10 carbons inclusive.

In the above process 7-ADCA is first silylated by reaction with a silylating agent in an inert substantially anhydrous aprotic solvent.

Suitable solvents for the silylation reaction include such inert substantially anhydrous organic solvents as methylene chloride, tetrahydrofuran, chloroform, tetrachloroethane, nitromethane, benzene and diethyl ether. A preferred solvent is methylene chloride.

Silylating agents useful in the above process are known in the art [see, for example, U.S. Pat. Nos. 3,654,266, 3,575,970, 3,499,909, 3,349,622, 3,595,855, 3,249,622 and U.K. Pat. Nos. 1,339,605, 959,853 and 1,008,468[. While any known silylating agent may be employed, it is preferred to use an agent selected from those of the formula

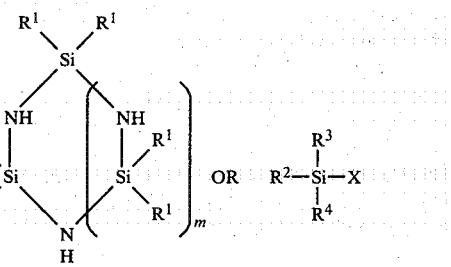

wherein $R^2$, $R^3$ and $R^4$ are hydrogen, halogen, (lower) alkyl, halo(lower)alkyl, phenyl, benzyl, tolyl or dimethylaminophenyl, at least one of the said $R^2$, $R^3$ and $R^4$ groups being other than halogen or hydrogen; $R^1$ is (lower)alkyl; m is an integer of 1 to 2 and X is halogen or

wherein $R^5$ is hydrogen or (lower)alkyl and $R^6$ is (lower)alkyl or

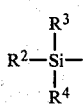

wherein $R^2$, $R^3$ and $R^4$ are as defined above.

Examples of suitable silylating agents include trimethylchlorosilane, hexamethyldisilazane, triethylchlorosilane, methyltrichlorosilane, dimethyldichlorsilane, triethylbromosilane, tri-n-propylchlorosilane, bromomethyldimethylchlorosilane, tri-n-butylchlorosilane, methyldiethylchlorosilane, dimethylethylchlorosilane, phenyldimethylbromosilane, benzylmethylethylchlorosilane, phenylethylmethylchlorosilane, triphenylchlorosilane, triphenylfluorosilane, tri-o-tolylchlorosilane, tri-p-dimethylaminophenylchlorosilane, N-ethyltriethylsilylamine, hexaethyldisilazane, triphenylsilylamine, tri-n-propylsilamine, tetraethyldimethyldisilazane, tetramethyldiethyldisilazane, tetramethyldiphenyldisilazane, hexaphenyldisilazane and hexa-p-tolyldisilazane. Other suitable silylating agents are hexaalkylcyclotrisilazanes or octa-alkylcyclotetrasilazanes and silylamides and silylureides such as trialkylsilylacetamide and a bis-trialkylsilylacetamide. The most preferred silylating agents are trimethylchlorosilane and hexamethyldisilazane.

Where a silyl halide, e.g. trimethylchlorosilane, is employed as the silylating agent, the silylation step is carried out in an inert, substantially anhydrous, aprotic solvent in the presence of an acid (hydrogen halide) acceptor, preferably a nitrogen base such as triethylamine, dimethylamine, dimethylaniline, quinoline, lutidine or pyridine. Preferred acid acceptors are triethylamine or a mixture of triethylamine and dimethylaniline. Where a silazane, e.g. hexamethyldisilazane, is employed, the silylation step is conveniently effected by heating the silazane and 7-ADCA so that ammonia or amine derivatives formed as by-products of the reaction are distilled off.

In preparing silylated 7-ADCA in the above process, theoretically from one to two molar equivalents of silylating agent can be employed per mole of 7-ADCA to give mono- or disilylated 7-ADCA or mixtures thereof. Thus, when 7-ADCA is reacted with about one equivalent of silylating agent, there is formed monosilylated 7-ADCA. In the case where trimethylchlorosilane or hexamethyldisilazane are used, for example, the product has the formula

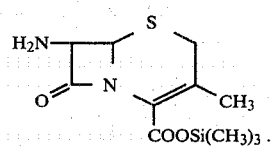

The disilyl derivative of 7-ADCA may be prepared by employing in the silylation step at least two equivalents of silylating agent per mole of 7-ADCA. When the preferred trimethylchlorosilane or hexamethyldisilazane are used, disilylated 7-ADCA is formed having the formula

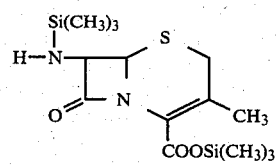

The silylation step may be conducted over a wide temperature range, e.g. room temperature up to the reflux temperature of the solvent system. Advantageous results are generally obtained at room temperature with the silyl halides (20°-30° C.) and with elevated temperatures, e.g. reflux temperature, in the case of the silazanes which are generally less active.

Either the mono- or disilylated 7-ADCA or a mixture thereof may then be acylated with D(−)-α-amino-α-(p-hydroxyphenyl)acetyl chloride hydrochloride (most preferably in the form of the hemidioxane solvate disclosed in U.S. Pat. No. 3,925,418) to form in situ a silylated cefadroxil intermediate. Any silyl groups present after acylation are then removed by hydrolysis or alcoholysis and the desired cefadroxil end-product recovered from the reaction medium, e.g. by neutralization to the isoelectric point whereupon the cefadroxil precipitates out of solution.

The solvents employed in acylation of the silylated 7-ADCA are defined above in connection with silylation step (a).

A preferred temperature range for the acylation step is from about $-20°$ C. to about $+70°$ C. The temperature is not critical, however, and temperatures higher or lower than those within the preferred limits may be used. The most preferred acylation temperature is between about $-10°$ and $+10°$ C.

The acylation procedure is preferably carried out in the presence of an acid acceptor which may be the same as or different from that employed in preparing the silylated 7-ADCA. Best results are obtained if a weaker (i.e. $pK_a \leq 7$) tertiary amine base such as dimethylaniline, pyridine or quinoline is used. Preferably, there is also incorporated a mineral acid salt of a weak tertiary amine, e.g. the hydrochloride salt of dimethylaniline, so as to inactivate any excess amine (see, e.g. U.S. Pat. No. 3,678,037).

While some reaction will occur regardless of the molar proportion of reactants used, it is preferred in order to obtain maximum yields in the acylation step to use about one mole of acylating agent or a slight molar excess thereof per mole of silylated 7-ADCA.

The silylated cefadroxil acylation product is treated by hydrolysis or alcoholysis to cleave the silyl protecting groups. Thus, the silylated intermediate may be hydrolyzed by addition of water, or, more preferably, alcoholized by addition of a suitable alcohol, preferably a $C_1$-$C_4$ alkanol such as methanol, ethanol, n-propanol, isopropanol, n-butanol, etc. A mixture of water and a lower alkanol ($C_1$-$C_4$) may also be employed in the cleavage step.

Cefadroxil may be recovered from the reaction solution by methods customarily employed for the isolation of similar cephalosporins. Thus, the product may be recovered as the neutral molecule by upwardly adjusting the pH of the reaction mixture until the desired acid precipitates from solution. Preferably a non-aqueous amine base such as triethylamine is used. Cefadroxil in the form of the free acid may be converted to a pharmaceutically acceptable carboxylic acid or acid addition salt by reaction with an appropriate base or acid.

According to a preferred embodiment of the invention, 7-aminodesacetoxycephalosproanic acid is silylated with hexamethyldisilazane in a substantially anhydrous aprotic solvent, preferably methylene chloride, with external heating, preferably at the reflux temperature of the solvent, to form in situ disilyated 7-ADCA of the formula

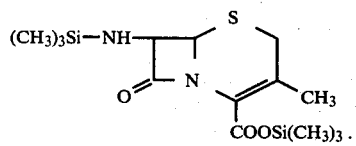

The disilylated 7-ADCA is then acylated directly in the same solution (preferably at $-10°$ to $-10°$ C.) with the $D(-)$-$\alpha$-amino-$\alpha$-(p-hydroxyphenyl)acetyl chloride hydrochloride, preferably in the form of the hemidioxane solvate, in the presence of an acid acceptor, preferably a tertiary amine base having a $pK_a \leq 7$ such as dimethylaniline, pyridine or quinoline. Following acylation, the silylated cefadroxil acylation product is treated with a $C_1$-$C_4$ alkanol, preferably methanol or n-butanol, to cleave any silyl groups and the product is recovered (after an optional filtration step) by neutralization to the isoelectric point with a tertiary amine base preferably triethylamine, to effect precipitation.

Use of hexamethyldisilazane as the silylating agent in place of the usual silyl halides such as trimethylchlorosilane eliminates the formation of an acid halide by-product and, consequently, the necessity of employing an acid acceptor in the silylation step. Without the presence in the reaction medium of this acid acceptor, less insoluble salt, e.g. triethylamine.HCl, is present to interfere with the later recovery steps. By use of hexamethyldisilazane, therefore, higher yields of cefadroxil are achievable than with the conventional trimethylchlorosilane silylation.

In another aspect the present invention provides a novel crystalline monohydrate form of cefadroxil which has been found to be a stable useful form of the cephalosporin antibiotic particularly suitable for pharmaceutical formulations.

The crystalline cefadroxil monohydrate of this invention exhibits essentially the following x-ray powder diffraction properties:

| Line | Spacing d(Å) | Relative Intensity |
|------|-------------|-------------------|
| 1 | 8.84 | 100 |
| 2 | 7.88 | 40 |
| 3 | 7.27 | 42 |
| 4 | 6.89 | 15 |
| 5 | 6.08 | 70 |
| 6 | 5.56 | 5 |
| 7 | 5.35 | 63 |
| 8 | 4.98 | 38 |
| 9 | 4.73 | 26 |
| 10 | 4.43 | 18 |
| 11 | 4.10 | 61 |
| 12 | 3.95 | 5 |
| 13 | 3.79 | 70 |
| 14 | 3.66 | 5 |
| 15 | 3.55 | 12 |
| 16 | 3.45 | 74 |
| 17 | 3.30 | 11 |
| 18 | 3.18 | 14 |
| 19 | 3.09 | 16 |
| 20 | 3.03 | 29 |
| 21 | 2.93 | 8 |
| 22 | 2.85 | 26 |
| 23 | 2.76 | 19 |
| 24 | 2.67 | 9 |
| 25 | 2.59 | 28 |
| 26 | 2.51 | 12 |
| 27 | 2.46 | 13 |
| 28 | 2.41 | 2 |
| 29 | 2.35 | 12 |
| 30 | 2.30 | 2 |
| 31 | 2.20 | 15 |
| 32 | 2.17 | 11 |
| 33 | 2.12 | 7 |
| 34 | 2.05 | 4 |
| 35 | 1.99 | 4 |
| 36 | 1.95 | 14 |
| 37 | 1.90 | 10 |

The details for this determination of x-ray diffraction properties are as follows:

A small amount of each sample was sealed in either a 0.2 mm. or a 0.5 mm. diameter low scattering glass capillary tube which was mounted for exposure in a 114.6 mm. diameter Debye-Scherrer powder diffraction camera. Exposure time was 3 hours on a Norelco X-Ray Generator operated at 35 KV $-20$ mA using a standard focus copper target x-ray tube (weighted Cu $K_\alpha$ wavelength $\lambda = 1.5418$ Å). Kodak No-Screen X-Ray Film was used and developed for 3 minutes at 20° C. in Kodak Liquid X-Ray Developer.

A very small amount of crystalline sodium fluoride was mixed in with some samples to provide internal calibration. In addition, a sample of pure NaF was run through the complete procedure for the same purpose.

The films were read on a Norelco Debye-Scherrer film reader, recording the positions of the diffraction rings to the nearest 0.05 mm. The data were corrected for film shrinkage and the interplanar spacings (d-spacings) were calculated from the corrected data. A computer program (XRAY, by P. Zugenmaier) was used for all calculations. The accuracy in the resulting d-spacing data was ~1%.

An intensity record of all films was obtained using a Joyce-Loeble Mark IIIC Recording microdensitometer (scan ratio 5:1, 0.1 O.D. wedge). Relative intensities on a scale 1-100 were assigned to all recognizable diffraction rings using peak intensities corrected for the background reading.

A sample of the crystalline monohydrate product was subjected to infrared analysis and the spectrum of the sample (as KBr disc) is shown in FIG. 1.

A further provision of the present invention is a process for preparing the above-described crystalline cefadroxil monohydrate, which process comprises (a) silylating 7-aminodesacetoxycephalosporanic acid in an inert substantially anhydrous aprotic solvent;

(b) acylating the so-produced silylated 7-aminodesacetoxycephalosporanic acid with D(−)-α-amino-α-(p-hydroxyphenyl)acetyl chloride hydrochloride in an inert substantially anhydrous aprotic solvent in the presence of an acid acceptor;

(c) cleaving any silyl groups of the acylation product by hydrolysis or alcoholysis; and (d) forming the desired monohydrate product by a method selected from (1) upwardly adjusting the pH of the solution from step (c) in the presence of excess dimethylformamide to form the dimethylformamide solvate of 7-[D-α-amino-α-(p-hydroxyphenyl)acetamido]-3-methyl-3-cephem-4-carboxylic acid; dissolving said dimethylformamide solvate in acidified water or a mixture of acidified water and acetonitrile, and upwardly adjusting the pH of said acidified solution to precipitate the desired crystalline monohydrate;

(2) upwardly adjusting the pH of the solution from step (c) in the presence of excess dimethylformamide to form the dimethylformamide solvate of 7-[D-α-amino-α-(p-hydroxyphenyl)acetamido]-3-methyl-3-cephem-4-carboxylic acid and contacting said dimethylformamide solvate with water or a partially aqueous medium to precipitate the desired crystalline monohydrate; or (3) upwardly adjusting the pH of the solution from step (c) to form 7-[D-α-amino-α-(p-hydroxyphenylacetamido]-3-methyl-3-cephem-4-carboxylic acid and contacting said acid with water or a partially aqueous medium to effect crystallization of the desired monohydrate.

In preparing crystalline cefadroxil monohydrate according to the above process, the silylation, acylation and silyl group cleavage steps are carried out as described previously in connection with the improved acylation procedure for preparing cefadroxil.

The desired crystalline monohydrate may then be prepared according to any one of several alternative routes.

In one method, the solution of cefadroxil following the solvolysis step is neutralized with a basic substance, e.g. a tertiary amine base such as triethylamine, in the presence of excess dimethylformamide until the dimethylformamide solvate of cefadroxil precipitates from solution. The solvate may then be collected and washed (preferably not dried) to give a crystalline material identical to that disclosed in U.S. Pat. No. 3,985,741 (Example 6A). Cefadroxil dimethylformamide solvate may be converted to the desired cefadroxil monohydrate by dissolving the solvate in acidified water or a mixture of acidified water and acetonitrile and then neutralizing the acidified solution to precipitate the monohydrate product.

Dissolution of the cefadroxil dimethylformamide solvate occurs at a pH of around 2-2.4 which can be achieved by addition of a mineral acid, e.g. HCl, to a mixture of the solvate in either water or an acetonitrile-water mixture. Solid impurities may be removed at this stage of the process by filtration of the acidified solution after treatment with activated carbon and/or filter aid.

The acidified solution is then neutralized, preferably with agitation and with warming to about 35°-60° C., by addition of a suitable base, e.g. an aliphatic tertiary amine such as triethylamine, to raise the solution pH to the point where cefadroxil monohydrate crystallizes from solution.

Acetonitrile is preferably added to the solution as an antisolvent (precipitating agent) during neutralization to achieve maximum recovery of the desired product. Yields are also improved by seeding the solution with seed crystals of the desired monohydrate prior to and-/or during the final neutralization step.

An alternative method for preparing the crystalline cefadroxil monohydrate in the above process involves preparing cefadroxil dimethylformamide solvate as described above and contacting said solvate with water or a partially aqueous medium until the desired monohydrate crystallizes from the solvent system.

The cefadroxil dimethylformamide solvate is dissolved in water or a mixture of water and an organic solvent such as acetonitrile, acetone, a $C_1$-$C_5$ alkanol (methanol, ethanol, n-propanol, isopropanol, n-butanol, amyl alcohol, etc.), or a mixture thereof. The use of partially aqueous organic solvent systems is preferred since the organic solvents take up many of the impurities and result in a purer end-product.

When mixtures of water and organic solvents are employed, the ratios of the solvent components may be varied over a wide range without serious adverse effects. The preferred solvent ratios have been determined for several partially aqueous solvent systems and are as follows:

water:acetone (1:3) (v/v)
water:isopropanol (1:3) (v/v)
water:acetonitrile (1:3) (v/v)
water:n-butanol (1:1) (v/v).

With the water-acetonitrile system, it is preferred to add n-butanol (preferably after solubilization of the solvate) to ensure that the solvent system remains as a single homogeneous phase during crystallization. Preferably, sufficient n-butanol is added to this crystallization system so as to achieve a final solvent ratio of water-:acetonitrile:n-butanol (1:2:1) (v/v).

The concentration of solvate in the aqueous or partially aqueous crystallization medium is not critical. Best yields have been obtained, however, when concentrations of between about 400 and 800 grams/liter of solution are employed. The solvate is preferably added to the solvent system in increments and with stirring over a period of time which is dependent on the quantity of solvate used, i.e. from a few minutes up to several hours.

Crystallization may be carried out over a wide temperature range, i.e. from room temperature up to the boiling point of the solvent system. Good results are obtained in a temperature range of from about 35°–60° C., most preferably 40°–45° C.

Yields of monohydrate are improved by seeding the solution of dimethylformamide solvate with seed crystals of cefadroxil monohydrate.

Yet another method of preparing the desired monohydrate in the above process comprises (1) preparing the silylated cefadroxil and cleaving the silyl protecting groups by hydrolysis or alcoholysis as described above, (2) neutralizing the solution from the cleavage step to the isoelectric point of cefadroxil (~pH 5.7–5.8) with a suitable base, preferably an aliphatic tertiary amine such as triethylamine, to precipitate impure or primary grade cefadroxil, and (3) contacting said impure cefadroxil with water or a mixture of water with a suitable organic solvent, preferably acetonitrile, acetone, a $C_1$–$C_5$ alkanol (e.g. methanol, ethanol, n-propanol, isopropanol, n-butanol, amyl alcohol, etc.) or mixture thereof, until cefadroxil monohydrate crystallizes from solution.

Neutralization of the cefadroxil solution to form impure or primary grade cefadroxil (amorphous) can be conveniently carried out at room temperature by gradual addition of the base to the stirred solution. The impure cefadroxil may then be crystallized in the same manner as described above for the cefadroxil dimethylformamide solvate. As in the case of the dimethylformamide solvate crystallization procedure, the most preferred solvent system is water:acetonitrile:n-butanol (1:2:1) (v/v).

A most preferred embodiment of the present invention is the process of preparing crystalline cefadroxil monohydrate from either cefadroxil dimethylformamide solvate or impure (primary grade) cefadroxil by the steps of (a) dissolving the dimethylformamide solvate of 7-[D-α-amino-α-(p-hydroxyphenyl)acetamido]-3-methyl-3-cephem-4-carboxylic acid in acidified water or a mixture of acidified water and acetonitrile; and upwardly adjusting the pH of said acidified solution until the desired monohydrate crystallizes from solution; or (b) contacting 7-[D-α-amino-α-(p-hydroxyphenyl)-acetamido]-3-methyl-3-cephem-4-carboxylic acid or the dimethylformamide solvate thereof with water or a partially aqueous medium until the desired monohydrate crystallizes from solution.

The dimethylformamide solvate and cefadroxil starting materials used in the above process may be prepared by the processes described in the present application or by other known processes, e.g. the processes disclosed in U.K. Pat. No. 1,240,687, U.S. Pat. No. 3,985,741 and Belgium Pat. No. 829,758.

Preferred conditions for forming cefadroxil monohydrate in the above process are as described above in connection with the previously disclosed overall reaction scheme, i.e. the combined silylation, acylation and monohydrate production steps.

By employing the preferred reaction conditions described above, the present invention makes possible the production of primary grade cefadroxil in yields of up to about 90% (activity yields) and subsequent conversion of said cefadroxil or its dimethylformamide solvate to cefadroxil monohydrate in activity yields of up to about 83%. Overall yields of cefadroxil monohydrate from 7-ADCA range up to about 75% without taking into account the additional ~5% yield possible if a second crop of monohydrate is recovered from the crystallization mother liquor as described below in Example 5.

The crystalline monohydrate prepared according to any of the above processes can be recovered by conventional methods, e.g. filtration, and then washed, dried and prepared into pharmaceutical formulations for use in antibiotic therapy in combatting various bacterial diseases. Examples of such formulations (e.g. capsules or tablets), doses and modes of administration of cefadroxil monohydrate and its pharmaceutical compositions are as described in U.S. Pat. Nos. 3,489,752 and 3,985,741 for the amorphous form of cefadroxil.

The invention thus includes a pharmaceutical composition, most preferably a pharmaceutical composition adapted for oral administration, comprising crystalline cefadroxil monohydrate with a suitable inert pharmaceutically acceptable carrier or diluent.

The invention further includes a method of treating humans or other animal species (e.g. mammals) for diseases caused by Gram-positive or Gram-negative bacteria, which method comprises administering to the subject host an effective dose of crystalline cefadroxil monohydrate as defined herein or a pharmaceutical composition as hereinbefore defined.

The following examples are given by way of illustration of the present invention. All temperatures are in degrees Centigrade. 7-Aminodesacetoxycephalosporanic acid is abbreviated as 7-ADCA, triethylamine as TEA, dimethylaniline as DMA and dimethylformamide as DMF.

EXAMPLE 1

Preparation of Crystalline Cefadroxil Monohydrate

A. Cefadroxil Dimethylformamide Solvate

To a three-necked flask equipped with a mixer and thermometer were added 2250 ml. of methylene chloride (K.F. 0.05%), 7-ADCA (100 g.), dimethylaniline (80.5 g.) and trimethylchlorosilane (105 g.). To this reaction mixture was then added 18.1 g. of triethylamine with agitation over a period of about 20–30 minutes. The temperature was maintained between 25°–27° during the TEA addition. The reaction mixture was stirred for 60 minutes at 25°–27° and 67 g. of a solution of methylene chloride containing 33% w/w of DMA.HCl (K.F.≦0.1%) was then added. The solution was brought to 4°–6° and 128.5 g. of D(−)-(p-hydroxyphenyl)glycyl chloride hydrochloride added in five equal aliquots, one aliquot being added every 10 minutes. Following addition of the acylating agent, the reaction mixture was stirred for an additional 60 minutes at 4°–6°. To the acylation mixture was then added 500 ml. of water and the solution was stirred for 20 minutes. The reaction mixture was filtered on Dicalite precoat (Great Lakes Carbon Corporation) and washed with 150 ml. water and 300 ml. methylene chloride. The aqueous phase was retained and to it at 20° was added 1100 ml. of isopropanol and sufficient triethylamine to bring the solution pH to 4.4–4.5. The solution was heated at 24°–26° and dimethylformamide (2250 ml.) added under slow agitation over a 20 minute period. After 60 minutes, the reaction mixture was cooled to 3° and agitated for an additional 120 minutes. The cefadroxil dimethylformamide solvate crystalized from solution and was collected by filtration and washed with 400 ml. of dimethylformamide.

B. Conversion of Cefadroxil DMF Solvate to Cefadroxil Monohydrate

Into a 2000 ml. beaker were added with agitation at 20°–25° water (225 ml.), acetonitrile (700 ml.), the cefadroxil dimethylformamide solvate wet cake (as obtained in part A), 10 g. of activated carbon (Darco KB manufactured by Atlas Chemical Industries, Inc.), 30 g. of Dicalite and sufficient 6 N HCl to effect dissolution of the reaction mixture (pH 2.0–2.4). The solution was stirred for 15 minutes and filtered on Dicalite. The precoat was washed with 460 ml. of a mixture containing 110 ml. water and 350 ml. acetonitrile. After heating the solution and washings to 35°–37°, there was added under agitation over a 10 minute period sufficient triethylamine to bring the pH to 2.2–2.3 and 600 ml. of aceonitrile. The solution was stirred at 35°–37° for 30–40 minutes. At the end of this period, 600 ml. of acetonitrile was added over a 10 minute period and then (with agitation) sufficient triethylamine over a 40 minute period to bring the pH to 4.4–4.5. The reaction mixture was stirred over a 30 minute period (35°–37°) followed by addition with agitation of 900 ml. acetonitrile over a 25 minute period while maintaining the temperature at 35°–37°. After 90 minutes the mixture was cooled to 20° and stirred over a 120 minute period. The crystals of cefadroxil monohydrate were collected by filtration, washed with 400 ml. of a mixture of 100 ml. water and 300 ml. acetonitrile and dried in an air oven for 16 hours. There was obtained 94.7 g. of crystalline cefadroxil monohydrate having the following characteristics:

Description: crystalline yellowish white powder
Infrared: as in FIG. 1
Moisture (K.F.): 5.1%
pH: 4.5
Specific Rotation: +158°
Chemical Assay (iodometric): 952 mcg./mg.
Biological Assay: 922 mcg./mg.

EXAMPLE 2

Preparation of Crystalline Cefadroxil Monohydrate

A. Cefadroxil Dimethylformamide Solvate

To a 6 liter reactor was added with stirring 3.5 l. of anhydrous methylene chloride, 7-ADCA (149.8 g.; 0.693 mole), trimethylchlorosilane (189 ml.; 1.5 mole) and dimethylaniline (87 g.; 0.717 mole). Triethylamine (196 ml.; 1.40 mole) was then added over 20 minutes with stirring at a temperature below 25°. The mixture was stirred for 1 hour at 20°–25° and then cooled to 0° to +5°. To the solution was added DMA.HCl (30% w/w in methylene chloride; 91 ml.; 0.717 moles) followed by D(−)-(p-hydroxyphenyl)glycyl chloride hydrochloride (177.6 g.; 0.64 mole) in 5 portions with stirring over one hour. The mixture was stirred 2 hours at 0° to +5° and then 70 ml. of methanol was added over 15 minutes followed by 800 ml. of water. After 15 minutes of stirring, the pH was adjusted to 2.3 with 120 ml. of TEA. The aqueous solution was separated, polish filtered on a Celite (tradename for diatomaceous earth manufactured by Johns-Manville Products Corporation) pad (washings=200 ml.) and adjusted to pH 4.5 with TEA. Isopropanol (1.7 l.) followed by DMF (3.4 l.) were then added. The cefadroxil DMF solvate crystallized after a few minutes and the suspension was then stirred 3 hours and left to stand overnight. The solid was collected, washed once with DMF and twice with acetone and dried 24 hours at 50° to yield 267 g.

Analytical Data

Specific Rotation: $\alpha_D$(1% $H_2O$) = +124°
Moisture (K.F.): 1.83%
Chemical Assay (iodometric): 765 mcg./mg.
Activity Yield: 80%
Infrared Spectrum: Identical with that disclosed in Example 6A. of U.S. Pat. No. 3,925,418.

B. Cefadroxil Monohydrate

Cefadroxil DMF solvate (50 g.; ~0.105 mole) was dissolved in 150 ml. water and 8.8 ml. HCl (36%). Charcoal (2.7 g.) and Celite (1.35 g.) were then added. After 30 minutes of stirring, the mixture was filtered through a Celite pad and washed with water. The filtered solution was heated to 40° and the pH adjusted to 2.5 with triethylamine. The mixture was then seeded with crystals of cefadroxil monohydrate and the pH adjusted to 4.5 with triethylamine. The suspension was stirred for one hour at 50° and progressively cooled to room temperature and then maintained for one hour at 0° to +5°. The crystalline cefadroxil monohydrate was collected, washed twice with cold water and dried at 40° to yield 30.8 g. (~76–77% yield) of product having the same physical characteristics as described in Example 1.

EXAMPLE 3

Preparation of Cefadroxil (illustrates most preferred silylation, acylation and recovery procedures)

To a slurry of 7-ADCA (1.0 kg.; 4.6 moles) 98.2% purity; K.F.=0.1%) in 3.5 liters of dry methylene chloride (KF≦0.01%) is added with moderate stirring 770 ml. (3.7 mole) of hexamethyldisilazane. The slurry is refluxed for 8 hours to effect solution and then refluxed for an additional 16 hours under an atmosphere of dry $N_2$. Dry methylene chloride is added to the reaction mixture to bring the total volume to about 8.5 liters. After cooling to ~20°–25° C., N,N′-dimethylaniline (DMA) (605 ml.; 4.7 moles) is added followed by addition of 467 ml. (0.95 mole) of a 32% w/v solution of DMA.HCl with moderate stirring. The reaction mixture is chilled to −5° to −7° C. At 10 minute intervals there is added 1310 g. (4.65 moles) of D(−)-p-hydroxyphenylglycyl chloride hydrochloride hemidioxane solvate in 5 increments of 262 g. each while holding the temperature at −5° C. The reactor is blanketed with dry $N_2$ gas and moderate stirring is continued for ~1.5 hours at −5° C. The reaction mixture is then warmed to 0°–3° C. and the reaction continued for 2–3 hours or until complete solution is obtained. The solution is then warmed to 20° C. and maintained at this temperature for 30–45 minutes. Following acylation, 3.75 liters of dry methanol is added as rapidly as possible while maintaining the temperature at 25°–30° C. After stirring for 10 minutes to ensure complete solution, the solution is polish filtered and the reactor washed with 930 ml. of dry methanol and 1860 ml. of dry methylene chloride. The wash is added to the filtrate to give a volume of ~17.5 liters. The filtrate is then titrated with triethylamine to pH ~2.8 (~450 ml. triethylamine) followed by continued slow addition of triethylamine over 30 minutes to precipitate out cefadroxil as a floculent amorphous product. The pH is adjusted with triethylamine until a pH of about 5.7–5.8 is reached (total TEA used is ~1500–1520 ml.). The slurry is stirred and cooled to 20°–22° C. as additional methylene chloride is added slowly so as to obtain a volume of 28 liters. The slurry is stirred for 30 minutes and filtered, washed with 4:1 methylene chloride:methanol and methylene chloride and dried at 45°–50° C. to give primary grade cefadroxil. The product is produced in yields of ~1640 g. per 1 kg. of 7-ADCA starting material and has a biopotency of ~900 mcg./mg. Assay indicates less than 2 ppm of dimethylaniline is present. The product has a very high water solubility.

An additional amount of cefadroxil product (~125 g.) may be recovered from the mother liquor and wash produced above by the steps of (1) reducing the volume of the filtrate to a mush, (2) adding 28 liters of methylene chloride to the mush and warming the slurry at reflux, (3) maintaining the slurry at reflux for ~25–30 minutes to form the amorphous product, (4) filtering the slurry, (5) washing the solid cake with methylene chloride and (6) drying the cake at 45°–50° C.

EXAMPLE 4

Preparation of Cefadroxil (illustrates silylation with trimethylchlorosilane)

To a slurry of 7-ADCA (21.4 g.) (97.4% pure), dry methylene chloride (250 ml.), dimethylaniline (18 ml.) and trimethylchlorosilane (26.1 ml.) was added 27 ml. of triethylamine over a 20 minute period while maintaining the temperature at 25°–30° C. The temperature was held at 25°–30° C. for 1.5 hours, and the reaction mixture then cooled to −5° to −7° C. A solution of DMA.HCl (11.0 ml.) 32% w/v) in methylene chloride was added followed by addition of 28.3 g. D(−)-p-hydroxyphenylglycyl chloride hydrochloride hemidioxane solvate in 7 increments of about 4 grams over a 40 minute period while maintaining the temperature at between −2° and +5° C. Dimethylformamide (1 ml.) was added followed by 100 ml. of dry methanol. The reaction mixture was stirred, filtered, and the filtrate adjusted to pH 5.9 with 35 ml. of triethylamine over a 30 minute period. To this slurry was added with stirring 150 ml. of methylene chloride. The slurry was filtered and the filter cake then washed with 200 ml. of 4:1 methylene chloride:methanol and 260 ml. methylene chloride and dried to give primary grade cefadroxil (34.75 g.). Biopotency=965 mcg./mg. Bioyield=94.6%.

EXAMPLE 5

Preparation of Cefadroxil Monohydrate (illustrates most preferred crystallization procedure using water:acetonitrile:n-butanol (1:2:1))

To a stirred solution of 370 ml. deionized water and 370 ml. of acetonitrile at 40°–45° C. there is slowly added 50–60 g. of primary grade cefadroxil (bioactivity=840 mcg./mg.) over a 10 minute period. The resulting clear solution is seeded with crystals of cefadroxil monohydrate. After stirring for ~10 minutes a crystal slurry forms which is stirred for an additional 5 minutes. Additional primary grade cefadroxil is slowly added (~40–50 g. added/5–6 minutes) until a total of 1000 g. cefadroxil has been added. The slurry is then stirred at 40°–45° C. for about 30 minutes. Acetonitrile (370 ml.) is slowly added over a 15 minute period to the crystal slurry and the slurry is stirred for an additional 5 minutes. n-Butanol (370 ml.) is slowly added to the slurry over a 15 minute period after which the slurry is stirred and cooled slowly over a one hour period to 25° C. The slurry is then cooled to 0° to +3° C. over a one hour period and maintained at this range for 30 minutes. The final solvent ratios of water-acetonitrile-n-butanol are 1:2:1. The slurry is filtered and the filter cake washed with ~1150 ml. of water:acetonitrile (1:3) (v/v) and dried at 50° C. for about 12 hours in a circulating air oven.

There is obtained 745 g. of white crystalline cefadroxil monohydrate. Biopotency=940 mcg./mg. K.F.=4.6%.

The activity in the filtrate above can be readily recovered as good quality cefadroxil dimethylformamide solvate which can be converted to additional cefadroxil monohydrate by repeating the above process after substituting an equivalent weight of cefadroxil.DMF solvate for the cefadroxil starting material used therein. This second crop recovery procedure is outlined below.

1. Under vacuum at below 50° C. concentrate the filtrate to a heavy syrup.
2. Add 430 ml. of DMF to the syrup and warm to 45° C. The mix is stirred to obtain complete homogenity. Seed with crystals of cefadroxil.DMF solvate and add 145 ml. of isopropanol. Stir and cool to 25° C. over 2 hours. The slurry is stirred at 20°–25° C. for 3 hours and then chilled to 0° to 3° C. and held for 3 hours.
3. Filter the slurry and wash the cake with ~200 ml. of DMF.
4. Wash the cake with 500 ml. of acetone.
5. Dry the cake at 45°–50° C. in a circulting air over for ~12 hours.
6. A yield of 91 g. of DMF solvate should be obtained. Biopotency=~750 mcg./mg.
7. The DMF solvate if used as starting material in the process of Example 5 can be converted to cefadroxil monohydrate in 86.7% yield based on biopotency. Biopotency=925. K.F.=5.0%. Thus, an additional ~64 g. of monohydrate can be obtained which indicates ~90% total yield of monohydrate from the primary grade cefadroxil.

EXAMPLE 6

Cefadroxil Monohydrate (water-acetonitrile-n-butanol system)

Primary grade cefadroxil (27.0 g.) (prepared according to Example 4) was crystallized from a water-acetonitrile-n-butanol solvent system according to the following profile:

| Increment of Cefadroxil Added (in grams) | Time (in min.) | Temperature (°C.) | |
| --- | --- | --- | --- |
| 2 | 0 | 50 | initial solvent system comprised 10 ml. water and 4 ml. acetonitrile |
| 2 | 6 | 50 | seeded with crystals of cefadroxil . H$_2$O |
| 2 | 12 | 50 | 6 ml. acetonitrile added |
| 2 | 17 | 50 | |
| 2 | 23 | 45 | |
| 2 | 29 | 47 | |
| 2 | 36 | 50 | |
| 2 | 42 | 51 | |
| 2 | 47 | 52 | 3 ml. acetonitrile added |
| 2 | 58 | 51 | |
| 2 | 63 | 50 | |
| 2 | 69 | 47 | 2 ml. acetonitrile |

| Increment of Cefadroxil Added (in grams) | Time (in min.) | Temperature (°C.) | |
|---|---|---|---|
| | | | added |
| 2 | 79 | 47 | |
| 1 | 83 | 49 | 1 ml. acetonitrile added |
| | 98 | 47 | 4 ml. acetonitrile added |
| | 118 | 42 | 10 ml. n-butanol added - hot plate turned off |
| | 178 | 27 | |
| | 198 | 15 | |
| | 218 | 12 | |
| | 278 | 3 | filtered |

A total of 20 ml. of acetonitrile and 10 ml. n-butanol were used. The crystal slurry was filtered, and the filter cake was washed with 30 ml. of acetonitrile:water (3:1) (v/v) and dried to give 22.0 g. (81.3%) of monohydrate product. Biopotency=960 mcg./mg.

EXAMPLE 7

Cefadroxil Monohydrate (crystallization from water)

Cefadroxil (28 g.) (primary grade) was incrementally added to warmed (55° C.) water and crystallized according to the following profile:

| Increment of Cefadroxil Added (in grams) | Time (in min.) | Temperature (°C.) | |
|---|---|---|---|
| 2 | 0 | 55 | 25 ml. water used initially |
| 2 | 6 | 55 | seeded with crystals of cefadroxil . H₂O |
| 1 | 9 | 55 | |
| 1 | 14 | 55 | |
| 3 | 29 | 52 | |
| 4 | 39 | 52 | |
| 2 | 44 | 52 | |
| 2 | 46 | 52 | |
| 1 | 49 | 52 | 10 ml. water added |
| 3 | 54 | 52 | |
| 1 | 59 | 52 | |
| 2 | 64 | 52 | |
| 1 | 69 | 52 | 10 ml. water added |
| 2 | 74 | 52 | |
| 1 | 79 | 52 | 5 ml. water added Heating stopped. Allowed to cool to room temp. Placed in ice bath and stirred for ∼ 1 more hour. |

A total of 50 ml. water was used. The crystal slurry was filtered, and the filter cake was washed with 35 ml. of ice water and dried to give 20.65 g. (79%) of title product. Biopotency=960 mcg./mg. DMA<2 ppm. K.F.=4.6%. Klett color=375 (10% soln.). Chemical potency=963 mcg./mg.

EXAMPLE 8

Cefadroxil Monohydrate (crystallization from water-acetonitrile) Primary grade cefadroxil (8.0 g.) was added in 1 gram increments to a mixture of 5 ml. water and 5 ml. acetonitrile at 40° C. over a 45 minute period. The solution was seeded initially by addition of cefadroxil.H₂O crystals. The reaction mixture was stirred for 15 minutes followed by addition of 10 ml. acetonitrile over 15 minutes. The crystal slurry was allowed to cool to room temperature (approximately 3 hours) and was then filtered. The filter cake was washed with 7 ml. of acetonitrile:water (3:1) and dried to give 6.25 g. (81.5%) of title product. Biopotency=950 mcg./mg. K.F.=4.7%. Chemical potency=965 mcg./mg.

EXAMPLE 9

Cefadroxil Monohydrate (crystallization from butanol-water)

Primary grade cefadroxil (11.7 g.) was added to a 48° C. mixture of 8.35 ml. water and 7.0 ml. n-butanol in 1 g. increments over a two hour period. The reaction mixture was initially seeded with crystals of cefadroxil.H₂O and was stirred during the two hour addition step. The crystal slurry was allowed to cool to room temperature (approximately two hours) and was filtered. The filter cake was washed with n-butanol, water and isopropanol and dried to give 9.4 g. (82.7%) of title product. Biopotency=940 mcg./mg. K.F.=5.3%. Chemical potency=966 mcg./mg.

EXAMPLE 10

Cefadroxil Monohydrate (from cefadroxil.DMF solvate using water-acetonitrile-n-butanol crystallization)

Cefadroxil dimethylformamide solvate (27.0 g.) was incrementally added to a stirred solvent system initially comprising 10 ml. water and 3 ml. acetonitrile and crystallized according to the following profile:

| Increment of Cefadroxil . DMF Added in grams | Time (in min.) | Temperature (°C.) | |
|---|---|---|---|
| 2 | 0 | 25 | |
| 2 | 4 | 45 | seeded with cefadroxil . H₂O 2 ml. acetonitrile added |
| 2 | 13 | 42 | |
| 2 | 23 | 45 | 5 ml. acetonitrile added |
| 2 | 33 | 43 | |
| 2 | 39 | 42 | |
| 2 | 44 | 42 | |
| 2 | 50 | 42 | |
| 2 | 57 | 42 | |
| 2 | 65 | 42 | |
| 2 | 71 | 43 | |
| 2 | 83 | 43 | |
| 2 | 90 | 42 | |
| 1 | 98 | 42 | |
| | 128 | 42 | 10 ml. acetonitrile added |
| | 156 | 39 | 10 ml. n-butanol added |
| | 198 | 27 | ice bath cooling |
| | 263 | | filtered |

A total of 20 ml. acetonitrile and 10 ml. n-butanol were used. The crystal slurry was filtered and the filter cake washed with 30 ml. of acetonitrile:water (4:1). Upon drying of the cake, there was obtained 18.85 g. (86.7%) of monohydrate product. Biopotency=925 mcg./mg. K.F.=5.0%. DMF=0.1%; acetonitrile=0.2%; n-butanol=0.1%. Klett color=98 (10% soln.). Chemical potency=963 mcg./mg.

EXAMPLE 11

Cefadroxil Monohydrate (crystallization from water-isopropanol)

Primary grade cefadroxil (700 g.) was incrementally added to a stirred solvent system initially comprising 260 ml. water and 260 ml. isopropanol and crystallized according to the following profile:

| Increment of Cefadroxil Added (in grams) | Time (in min.) | Temperature (°C.) | |
|---|---|---|---|
| 56.26 | 0 | 45 | seeded with cefadroxil . H$_2$O |
| 57.87 | 4 | 50 | |
| 56.00 | 11 | 45 | |
| 69.62 | 20 | 55 | |
| 67.95 | 28 | 57 | |
| 64.93 | 39 | 54 | |
| 70.82 | 55 | 48 | |
| 64.11 | 65 | 44 | |
| 17.00 | 70 | 42 | |
| 72.41 | 110 | 47 | |
| 52.87 | 120 | 50 | |
| 28.90 | 128 | 50 | |
| 21.08 | 135 | 49 | |
| | 155 | 42 | |
| | 160 | 42 | 260 ml. isopropanol added |
| | 177 | 41 | 260 ml. isopropanol added |
| | 290 | | ice bath |
| | 325 | 17 | filtered |

A total of 780 ml. isopropanol was used. The crystal slurry was filtered and the filter cake washed with 800 ml. of isopropanol:water (3:1). Since the cake appeared dark in color, it was reslurried twice in 800 ml. isopropanol: water (3:1), filtered, washed (3:1 isopropanol-water) and dried to give 520.95 g. of title product. Biopotency=955 mcg./mg. K.F.=5.0%. Klett color=226 (10% soln.). Isopropanol=1.2%. Chemical potency=917 mcg./mg.

EXAMPLE 12

Cefadroxil Monohydrate (crystallization from water-acetonitrile-n-butanol)

Primary grade cefadroxil (700 g.) was incrementally added to a stirred solvent system initially comprising 260 ml. water and 260 ml. acetonitrile according to the following profile:

| Increment of Cefadroxil Added (in grams) | Time (in min.) | Temperature (°C.) | |
|---|---|---|---|
| 17.72 | 0 | 25 | |
| 15.67 | 5 | 25 | |
| 30.01 | 10 | 45 | seeded with cefadroxil . H$_2$O |
| 23.94 | 17 | 45 | |
| 26.06 | 25 | 45 | |
| 33.67 | 29 | 44 | |
| 35.28 | 37 | 43 | |
| 34.66 | 43 | 41 | |
| 41.80 | 49 | 40 | |
| 43.22 | 59 | 37 | |
| 55.00 | 68 | 35 | |
| 55.70 | 77 | 35 | |
| 54.70 | | | |
| 52.94 | | | |
| 54.94 | 108 | 35 | |
| 55.71 | 228 | 30 | |
| 46.00 | 253 | 30 | |
| | 323 | | 260 ml. acetonitrile added |
| | 333 | | 260 ml. n-butanol added |
| | 413 | 26 | ice bath |
| | 473 | 3 | filtered |

A total of 520 ml. acetonitrile and 260 ml. n-butanol were used. The crystal slurry was filtered and the filter cake washed with 100 ml. of acetonitrile:water (3:1) and 700 ml. of acetonitrile:water (4:1). Upon drying, the cake yielded 521.5 g. (83.5%) of monohydrate product. Biopotency=905 mcg./mg. K.F.=4.6%. Klett color=97 (10% soln.). Acetonitrile=0.5%. n-Butanol=0.1%. Chemical potency=940 mcg./mg.

EXAMPLE 13

Cefadroxil Monohydrate (crystallization from water-acetone)

Primary grade cefadroxil (700 g.) was incrementally added to a stirred solvent system initially comprising 260 ml. water and 260 ml. acetone and crystallized according to the following profile:

| Increment of Cefadroxil Added (in grams) | Time (in min.) | Temperature (°C.) | |
|---|---|---|---|
| 79.84 | 0 | 55 | seeded with cefadroxil . H$_2$O |
| 54.99 | 10 | 49 | |
| 54.43 | 18 | 47 | |
| 58.62 | 28 | 44 | |
| 61.60 | 39 | 44 | |
| 54.25 | 50 | 43 | |
| 58.39 | 62 | 43 | |
| 50.63 | 75 | 43 | |
| 53.11 | 89 | 43 | |
| 53.37 | 101 | 43 | |
| 50.59 | 113 | 43 | |
| 44.45 | 127 | 43 | |
| 27.07 | 137 | 42 | |
| | 154 | 42 | 260 ml. acetone added |
| | 169 | 39 | 260 ml. acetone added |
| | 274 | 26 | chilled to 10-12° and held for 1½ hours before filtration |

A total of 780 ml. acetone was used. The crystal slurry was filtered and the filter cake then washed with 900 ml. acetone:water (3:1) and dried to give 507.21 g. of title product. Biopotency=945 mcg./mg. K.F.=5.2%. Klett color=190 (10% soln.). Acetone=1.47%. Chemical potency=928 mcg./mg.

We claim:

1. A process for the preparation of crystalline 7-[D-α-amino-α-(p-hydroxyphenyl)acetamido]-3-methyl-3-cephem-4-carboxylic acid monohydrate exhibiting essentially the following x-ray diffraction properties:

| Line | Spacing d(A) | Relative Intensity |
|------|--------------|--------------------|
| 1  | 8.84 | 100 |
| 2  | 7.88 | 40 |
| 3  | 7.27 | 42 |
| 4  | 6.89 | 15 |
| 5  | 6.08 | 70 |
| 6  | 5.56 | 5 |
| 7  | 5.35 | 63 |
| 8  | 4.98 | 38 |
| 9  | 4.73 | 26 |
| 10 | 4.43 | 18 |
| 11 | 4.10 | 61 |
| 12 | 3.95 | 5 |
| 13 | 3.79 | 70 |
| 14 | 3.66 | 5 |
| 15 | 3.55 | 12 |
| 16 | 3.45 | 74 |
| 17 | 3.30 | 11 |
| 18 | 3.18 | 14 |
| 19 | 3.09 | 16 |
| 20 | 3.03 | 29 |
| 21 | 2.93 | 8 |
| 22 | 2.85 | 26 |
| 23 | 2.76 | 19 |
| 24 | 2.67 | 9 |
| 25 | 2.59 | 28 |
| 26 | 2.51 | 12 |
| 27 | 2.46 | 13 |
| 28 | 2.41 | 2 |
| 29 | 2.35 | 12 |
| 30 | 2.30 | 2 |
| 31 | 2.20 | 15 |
| 32 | 2.17 | 11 |
| 33 | 2.12 | 7 |
| 34 | 2.05 | 4 |
| 35 | 1.99 | 4 |
| 36 | 1.95 | 14 |
| 37 | 1.90 | 10 | which process comprises
(a) silylating 7-aminodesacetoxycephalosporanic acid in an inert substantially anhydrous aprotic solvent;
(b) acylating the so-produced silylated 7-aminodesacetoxycephalosporanic acid with D(−)-α-amino-α-(p-hydroxyphenyl)acetyl chloride hydrochloride in an inert substantially anhydrous aprotic solvent in the presence of an acid acceptor;
(c) cleaving any silyl groups of the acylation product by hydrolysis or alcoholysis; and
(d) forming the desired monohydrate product by upwardly adjusting the pH of the solution from step (c) to form 7-[D-α-amino-α-(p-hydroxyphenyl)acetamido]-3-methyl-3-cephem-4-carboxylic acid and contacting said acid with water or a partially aqueous medium to effect crystallization of the desired monohydrate.

2. A process as claimed in claim 1 wherein the silylation step (a) is accomplished by reacting 7-aminodesacetoxycephalosporanic acid with a silylating agent selected from those of the formulae

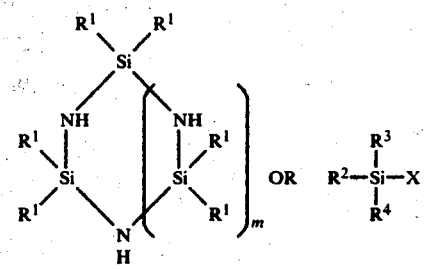

wherein $R^2$, $R^3$ and $R^4$ are hydrogen, halogen, (lower)alkyl, halo(lower)alkyl, phenyl, benzyl, tolyl or dimethylaminophenyl, at least one of the said $R^2$, $R^3$ and $R^4$ groups being other than halogen or hydrogen; $R^1$ is (lower)alkyl; m is an integer of 1 to 2 and X is halogen or

wherein $R^5$ is hydrogen or (lower)alkyl and $R^6$ is (lower)alkyl or

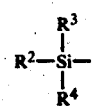

wherein $R^2$, $R^3$ and $R^4$ are as defined above.

3. A process as claimed in claim 2 wherein the silylating agent in step (a) is trimethylchlorosilane or hexamethyldisilazane.

4. A process as claimed in claim 1 wherein disilylated 7-aminodesacetoxycephalosporanic acid is produced in step (a) by using at least two equivalents of silylating agent per mole of 7-aminodesacetoxycephalosporanic acid.

5. A process as claimed in claim 1 wherein step (a) is carried out by silylating 7-aminodesacetoxycephalosporanic acid with trimethylchlorosilane in a substantially anhydrous aprotic solvent in the presence of an acid acceptor.

6. A process as claimed in claim 5 wherein the silylation step is carried out in a substantially anhydrous methylene chloride solvent system in the presence of an acid acceptor comprising triethylamine or a mixture of triethylamine and dimethylaniline at a temperature of about 20°–30° C.

7. A process as claimed in claim 1 wherein step (a) is carried out by silylating 7-aminodesacetoxycephalosporanic acid with hexamethyldisilazane in a substantially anhydrous aprotic solvent with external heating.

8. A process as claimed in claim 7 wherein the silylation step is carried out in a substantially anhydrous methylene chloride solvent at reflux temperature.

9. A process as claimed in claim 1 wherein acylation step (b) is carried out in a substantially anhydrous methylene chloride solvent system at a temperature in the range of from about −10° C. to +10° C. in the presence of an acid acceptor selected from a tertiary amine base having a $pK_a \leq 7$.

10. A process as claimed in claim 9 wherein the acid acceptor is dimethylaniline.

11. A process as claimed in claim 1 wherein in step (c) silyl groups are cleaved by treatment with water or a $C_1$–$C_4$ alkanol, or a mixture thereof.

12. A process as claimed in claim 1 wherein in step (c) silyl groups are cleaved by treatment with a $C_1$–$C_4$ alkanol.

13. A process as claimed in claim 1 wherein step (d) comprises
   (1) upwardly adjusting the pH of the solution from step (c) by addition of triethylamine to form 7-[D-α-amino-α-(p-hydroxyphenyl)acetamido]-3-methyl-3-cephem-4-carboxylic acid; and
   (2) contacting said cephalosporanic acid with a solvent system comprising water or a mixture of water with one or more organic solvents selected from acetonitrile, acetone or a $C_1$–$C_5$ alkanol until the desired monohydrate crystallizes from solution; and
   (3) recovering the desired monohydrate.

14. A process as claimed in claim 13 wherein the monohydrate crystallization step (2) is carried out at a temperature of from about 35°–60° C.

15. A process as claimed in claim 13 wherein the crystallization solvent system of step (2) comprises water:acetonitrile:n-butanol in a v/v ratio of 1:2:1.

16. A process as claimed in claim 13 wherein the crystallization solvent system of step (2) comprises water:acetone (1:3) (v/v), water:isopropanol (1:3) (v/v), water:acetonitrile (1:3) (v/v) or water:n-butanol (1:1) (v/v).

17. A process as claimed in claim 13 wherein seed crystals of the desired 7-[D-α-amino-α-(p-hydroxyphenyl)acetamido]-3-methyl-3-cephem-4-carboxylic acid monohydrate are added during the final crystallization step.

* * * * *